United States Patent
Dogu et al.

(10) Patent No.: US 11,253,444 B2
(45) Date of Patent: *Feb. 22, 2022

(54) ORAL CARE COMPOSITION

(71) Applicant: Colgate-Palmolive Company, New York, NY (US)

(72) Inventors: Nihal Dogu, Dayton, NJ (US); Kavita Vemishetti, Brooklyn, NY (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/309,402

(22) PCT Filed: Jun. 24, 2016

(86) PCT No.: PCT/US2016/039199
§ 371 (c)(1),
(2) Date: Dec. 12, 2018

(87) PCT Pub. No.: WO2017/222548
PCT Pub. Date: Dec. 28, 2017

(65) Prior Publication Data
US 2019/0209448 A1   Jul. 11, 2019

(51) Int. Cl.
| | | |
|---|---|---|
| *A61K 8/21* | (2006.01) | |
| *A61K 8/24* | (2006.01) | |
| *A61Q 11/00* | (2006.01) | |
| *A61K 8/34* | (2006.01) | |
| *A61K 8/19* | (2006.01) | |
| *A61K 8/27* | (2006.01) | |
| *A61K 8/362* | (2006.01) | |
| *A61K 8/365* | (2006.01) | |

(52) U.S. Cl.
CPC .............. *A61K 8/21* (2013.01); *A61K 8/19* (2013.01); *A61K 8/24* (2013.01); *A61K 8/27* (2013.01); *A61K 8/345* (2013.01); *A61K 8/362* (2013.01); *A61K 8/365* (2013.01); *A61Q 11/00* (2013.01)

(58) Field of Classification Search
CPC . A61K 8/24; A61K 8/365; A61K 8/20; A61K 2800/31; A61Q 11/00; A61P 31/04
See application file for complete search history.

(56) References Cited

U.S. PATENT DOCUMENTS

| | | | |
|---|---|---|---|
| 2,876,166 A | 3/1959 | Nebergall | |
| 4,349,533 A * | 9/1982 | Dent | A61K 8/26 424/49 |
| 4,961,924 A | 10/1990 | Suhonen | |
| 5,188,820 A | 2/1993 | Cummins et al. | |
| 6,685,920 B2 | 2/2004 | Baig et al. | |
| 6,696,045 B2 | 2/2004 | Yue et al. | |
| 6,702,999 B2 * | 3/2004 | Lawlor | A23G 3/346 424/48 |
| 8,906,347 B2 | 12/2014 | Strand et al. | |
| 8,906,349 B2 * | 12/2014 | Schaeffer-Korbylo | A61K 8/33 424/49 |
| 9,017,647 B2 | 4/2015 | Midha et al. | |
| 9,566,226 B2 | 2/2017 | Midha et al. | |
| 9,962,322 B2 | 5/2018 | Vemishetti et al. | |
| 9,968,803 B2 | 5/2018 | Fisher | |
| 10,154,948 B2 | 12/2018 | Vemishetti et al. | |
| 2008/0138298 A1 | 6/2008 | Glandorf et al. | |
| 2009/0214609 A1 | 8/2009 | Strand et al. | |
| 2013/0209375 A1 | 8/2013 | Moya Argilagos | |
| 2018/0221257 A1 | 8/2018 | Vemishetti et al. | |
| 2018/0243588 A1 | 8/2018 | Fisher | |
| 2018/0243589 A1 | 8/2018 | Fisher | |

FOREIGN PATENT DOCUMENTS

| | | |
|---|---|---|
| WO | 2008/041055 | 4/2008 |
| WO | 2008/102321 | 8/2008 |
| WO | 2015172345 | 11/2015 |

OTHER PUBLICATIONS

International Search Report and Written Opinion of the International Searching Authority in International Application No. PCT/US2016/039199, dated Sep. 30, 2016.

Shi, "Oral Clinical Pharmacy," People's Medical Publishing House, May 2012, p. 162.

Wen et al., "Practical Pediatric Dentistry", People's Military Medical Press, Jan. 2016, pp. 97-98.

* cited by examiner

*Primary Examiner* — Lezah Roberts

(57) ABSTRACT

The present invention relates to an oral care composition for use in the treatment or prevention of erosive tooth demineralization, plaque, and caries. This oral care composition includes zinc lactate dihydrate, a stannous ion source, at least one phosphate salt, and a buffer system.

6 Claims, No Drawings

ORAL CARE COMPOSITION

FIELD

The present invention relates to an oral care composition for use in the treatment or prevention of erosive tooth demineralization, plaque, and caries. This oral care composition includes zinc lactate dihydrate, a stannous ion source, at least one phosphate salt, and a buffer system.

BACKGROUND

Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization caused by acid produced from the bacterial degradation of fermentable sugar.

Oral care compositions which contain stannous ion sources exhibit excellent clinical benefits, particularly in the reduction of gingivitis and in the treatment or prevention of erosive tooth demineralization. However, there can be difficulty formulating oral care compositions with stannous ion sources. One reason is because the stannous ion can be unstable and may react with other ingredients of the oral care composition to form insoluble inactive tin compounds, thereby reducing the amount of available stannous ion in the composition. One way to overcome the stability problems with stannous ions is to limit the amount of water in the composition to very low levels, or to use a dual phase system. Both of these solutions to the stannous ion problem have drawbacks. Low water oral care compositions can be difficult to formulate with desired rheological properties, and dual-phase compositions are considerably more expensive to manufacture and package.

Thus, there is a need for providing improved stannous ion containing products for treating or preventing erosion of tooth enamel with antimicrobial effectiveness, reducing plaque or treating or controlling gingivitis.

BRIEF SUMMARY

Disclosed herein are oral care compositions comprising zinc lactate, a stannous ion source, at least one phosphate salt, and a buffer system. Methods and uses for this composition are also described throughout. The compositions disclosed herein provide improved protection from demineralization and enhanced antibacterial activity compared to the prior art.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

It has been surprisingly found that the inclusion of zinc lactate, a stannous source, a phosphate salt and a buffer system, selected at certain concentrations and amounts, is unexpectedly more efficacious in boosting the anti-erosion and anti-microbial properties of a stannous ions containing formulation when compared to certain prior commercial products which can contain stannous fluoride and zinc lactate.

In one aspect the present disclosure provides an oral care composition (Composition 1.0), comprising an orally acceptable carrier and:
  a. zinc lactate;
  b. a stannous ion source;
  c. a phosphate salt; and
  d. a buffer system; (e.g., wherein the buffer comprises trisodium citrate and citric acid).

In other embodiments of the first aspect, the present disclosure further provides:
  1.1 Composition 1.1, wherein the zinc lactate is zinc L-(+)-lactate, zinc D-(−)-lactate, zinc DL-lactate, or a combination thereof.
  1.2 Any of the preceding compositions, wherein the composition comprises zinc lactate dihydrate, e.g., zinc L-(+)-lactate dihydrate.
  1.3 Any of the preceding compositions, wherein the amount of zinc lactate is effective for protecting against dental erosion, dental caries, and periodontal problems such as gingivitis and periodontitis.
  1.4 Any of the preceding compositions, wherein the composition comprises zinc lactate from 0.05 to 10% by weight, e.g., 0.1 to 8%, 0.5 to 5%, 1 to 4%, 2 to 3%, or 2.5%, by weight of the oral care composition.
  1.5 Any of the preceding compositions, wherein the stannous ion source comprises a stannous halide (e.g., stannous fluoride or stannous chloride), a stannous carboxylate salt (e.g., stannous formate, acetate, gluconate, lactate, tartrate, oxalate, malonate or citrate), stannous ethylene glyoxide, or mixtures thereof.
  1.6 Any of the preceding compositions, wherein the stannous ion source (e.g., stannous fluoride) is present in an amount of from 0.01 to 5%, e.g., from 0.05 to 4%, 0.1 to 3%, 0.2 to 2%, 0.3 to 1%, 0.4 to 0.8%, 0.4 to 0.6% (e.g., or about 0.45% or about 0.454%), by weight of the oral care composition.
  1.7 Composition 1.5 or 1.6, wherein the stannous ion source is stannous fluoride.
  1.8 Composition 1.7, wherein the composition comprises stannous fluoride in an amount of from 0.01 to 5% by weight, e.g., 0.3 to 1%, (e.g., about 0.45% or about 0.454%) by total weight of the composition.
  1.9 Any of the preceding compositions, wherein the composition further comprises a fluoride ion source.
  1.10 The composition of 1.9, wherein the fluoride ion source is selected from: stannous fluoride, sodium fluoride, potassium fluoride, sodium monofluorophosphate, sodium fluorosilicate, ammonium fluorosilicate, amine fluoride, ammonium fluoride, and combinations thereof.
  1.11 The composition of 1.9 or 1.10, wherein the fluoride ion source is present in an amount from 0.01 to 5%, e.g., 0.1 to 3%, 0.2 to 2%, or 0.3 to 1%, (e.g., 0.45%) by total weight of the composition.
  1.12 Any of the preceding compositions, wherein the phosphate salt comprises orally acceptable mono- and/or polyphosphates for example, $P_{1-6}$ phosphates, or $P_{1-4}$ phosphates, such as orthophosphate (e.g., monobasic, dibasic or tribasic orthophosphate), pyrophosphates, tripolyphosphates, tetraphosphates, and hexaphosphates.
  1.13 Composition 1.12, wherein the phosphate salt is selected from alkali metal salts of monobasic, dibasic or tribasic phosphate, and alkali metal salts of polyphosphate, e.g., selected from sodium phosphate monobasic, potassium phosphate monobasic, sodium phosphate dibasic, potassium phosphate dibasic, sodium phosphate tribasic, potassium phosphate tribasic, tetrasodium pyrophosphate, tetrapotassium pyrophosphate, sodium tripolyphosphate, potassium tripolyphosphate and mixtures thereof.

1.14 Composition of 1.12 or 1.13, wherein the composition comprises phosphate salt in an amount of from 0.5 to 15% by weight, for example, from 1 to 10%, or 1 to 5% by weight (e.g., about 2% or about 3% by wt.).

1.15 Any of the preceding compositions, wherein the composition comprises one or more pyrophosphates or tripolyphosphates, such as tetrasodium pyrophosphate (TSPP) and/or sodium tripolyphosphate (STPP), for example, wherein the amount of TSPP is from about 0.5 to about 5% by weight (e.g., about 2% by weight), and/or wherein the amount of STPP is from 0.5 to 6% by weight (e.g., about 3% by weight), based on the weight of the composition.

1.16 Any of the preceding compositions, wherein the composition comprises TSPP and STPP, for example, wherein the amount of TSPP is from about 0.5 to about 10% by weight, e.g. 0.5 to 5%, or 1-3%, or about 2% by weight; and the amount of STPP is from 0.5 to 10% by weight, e.g., 0.5 to 6%, or 2-4%, or about 3% by weight; based on the weight of the composition.

1.17 Any of the preceding embodiments, wherein the composition is free of phosphates of more than four phosphates groups (e.g., free of hexaphosphates or hexametaphosphates).

1.18 Any of the preceding compositions, wherein the composition comprises one or more alkali metal orthophosphates, one or more alkali metal pyrophosphates and/or one or more alkali metal tripolyphosphates as the only phosphates, for example, a mixture of one or more of sodium phosphate (monobasic, dibasic or tribasic), tetrasodium pyrophosphate and trisodium polyphosphate as the only phosphates.

1.19 Any of the preceding compositions, wherein the only phosphates are alkali metal pyrophosphates and alkali metal tripolyphosphates, e.g., sodium pyrophosphate and sodium tripolyphosphate.

1.20 Any of the preceding compositions, wherein the composition comprises an aqueous buffer system, for example, wherein the buffer system comprises an organic acid and an alkali metal salt thereof, e.g., wherein the organic acid is citric acid and the salt is a mono-, di- and/or tri-alkali metal citrate salt, e.g., mono-, di- and/or tri-lithium, sodium, potassium, or cesium citrate salt, and citric acid. For example, where the composition comprises 1-10% by weight organic acid salt and 0.1-5% by weight organic acid.

1.21 Composition of 1.20, wherein the buffer system comprises tri-sodium citrate and citric acid (e.g., 1 to 10% by weight of the composition), for example, wherein the molar ratio of mono-, di- and/or tri-sodium citrate and citric acid is 1.5 to 5, (e.g., 2 to 4). The buffer system may be present, by weight, in an amount that is greater than the amount, by weight, of the source of stannous ions.

1.22 Any of the preceding compositions, wherein the composition has a pH from 5 to 8, e.g., from 6 to 8, or from 6 to 7, or from 7 to 8.

1.23 Any of the preceding compositions, wherein the composition comprises water in amount from 10 to 40% by weight, for example, 10-30%, or 10-20%, or 10-15%, (e.g., 12.7% by wt.) by weight of the oral care composition.

1.24 Any of the preceding compositions, further comprising one or more of abrasives, silica abrasives, surfactants, foaming agents, vitamins, polymers, enzymes, humectants, thickeners, additional antimicrobial agents, preservatives, sudsing agents, sweetening agents such as sodium saccharin, flavorings, aesthetics agents, colorings, and/or combinations thereof.

1.25 Any of the preceding compositions, wherein the composition comprises from 0.5-5% zinc lactate, 0.05-3% stannous fluoride, and 0.5-10% of phosphate salt, and a buffer system, by weight of the composition.

1.26 Any of the preceding compositions, wherein the composition comprises:
  a. About 2.5% zinc lactate
  b. About 3.6% citrate buffer (e.g., wherein the buffer is about 3.0% Trisodium Citrate and 0.6% Citric acid)
  c. About 0.45% Stannous fluoride (e.g., about 0.454%)
  d. About 3% sodium tripolyphosphate (STPP); and
  e. About 2% tetrasodium pyrophosphate (TSPP).

1.27 Any of the preceding compositions, wherein the composition is free of hexametaphosphate (e.g., sodium hexametaphosphate).

1.28 Any of the preceding compositions, wherein the composition is free of phosphates of more than four phosphate groups or free of phosphates of more than three phosphate groups.

1.29 Any of the preceding compositions, wherein the composition comprises sodium tripolyphosphate and tetrasodium pyrophosphate as the only phosphate compounds.

1.30 Any of the preceding compositions, wherein the composition comprises about 0.05 to 3% zinc ion, for example, 0.1 to 1%, or 0.25 to 0.75%, or about 0.6% zinc ion, by weight of the composition.

1.31 Any of the preceding compositions, wherein the composition does not further comprise zinc citrate, zinc phosphate, or zinc oxide.

1.32 Any of the preceding compositions wherein the zinc lactate is the only zinc ion source present.

1.33 Any of the preceding compositions which is a single-phase composition (e.g., not a dual phase composition).

1.34 Any of the preceding compositions which is effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.35 Any of the preceding oral compositions, wherein the oral composition is a toothpaste or a dentifrice, a mouthwash or a mouth rinse, a topical oral gel, or a denture cleanser.

1.36 A composition obtained or obtainable by combining the ingredients as set forth in any of the preceding compositions.

1.37 A composition for use as set for in any of the preceding compositions.

In another aspect, the present disclosure provides a method of improving oral health comprising applying an effective amount of the oral composition of any of the embodiments set forth herein (e.g., any of Compositions 1.0 et seq) to the oral cavity of a subject in need thereof, e.g., a method to i. reduce or inhibit formation of dental caries,
ii. reduce, repair or inhibit early enamel lesions, e.g., as detected by quantitative light-induced fluorescence (QLF) or electrical caries measurement (ECM),
iii. reduce or inhibit demineralization and promote remineralization of the teeth,
iv. reduce hypersensitivity of the teeth,
v. reduce or inhibit gingivitis,
vi. promote healing of sores or cuts in the mouth,
vii. reduce levels of acid producing bacteria,
viii. to increase relative levels of arginolytic bacteria,
ix. inhibit microbial bio film formation in the oral cavity,
x. raise and/or maintain plaque pH at levels of at least pH 5.5 following sugar challenge,
xi. reduce plaque accumulation,
xii. treat dry mouth,
xiii. enhance systemic health, including cardiovascular health, e.g., by reducing potential for systemic infection via the oral tissues,
xiv. Whiten teeth,
xv. reduce erosion of the teeth,
xvi. immunize (or protect) the teeth against cariogenic bacteria and their effects, and/or
xvii. clean the teeth and oral cavity.

"Phosphate" as used herein encompasses orally acceptable mono- and polyphosphates.

"Antibacterial activity" as used herein means activity as determined by any generally accepted in vitro or in vivo antibacterial assay or test.

Water:

Water employed in the preparation of oral compositions according to the present disclosure can be deionized (sometimes referred to as demineralized water) and/or free of organic impurities. As used herein, the amount of water in the compositions includes the free water which is added plus that amount which is introduced with other materials. The compositions may comprise water in amount from 10 to 40% by weight, e.g., from 10-30%, or 10-20%, or 10-15%; (e.g., 12.7% by wt.) by weight of the oral care composition. In a particular embodiment, the oral care composition of the present disclosure contains 12.7% by weight of water, which consists of 8.7% free water, in addition to the water included in the other ingredients added, such as Gantrez, Cocoamidopropyl betaine (CAPB), and glycerin.

Fluoride Source:

In various embodiments of the present disclosure, the composition further comprises fluoride ion source. This fluoride ion source may be in addition to any stannous fluoride present. Suitable fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. More examples of suitable fluoride ion yielding materials are provided in U.S. Pat. No. 3,535,421, to Briner et al.; and U.S. Pat. No. 3,678,154, to Widder et al, the disclosure of each of which is hereby incorporated by reference in their entirety.

Tartar Control Agents:

In various embodiments of the present disclosure (e.g., Composition 1.0 et seq), the compositions further comprise one or more anticalculus (tartar control) agents. Suitable anticalculus agents include without limitation mono-phosphates (e.g. monobasic, dibasic or tribasic phosphate) and $P_{1-6}$ polyphosphates (e.g., pyrophosphates, tripolyphosphate, tetraphosphates and hexametaphosphate salts), Gantrez® (a copolymer of methylvinyl ether (PVM) and maleic acid (MA)), polyaminopropanesulfonic acid (AMPS), polypeptides, polyolefin sulfonates, polyolefin phosphates, and diphosphonates. In certain embodiments, the other anticalculus agents are alkali and/or alkaline earth metal phosphate salts, for example, sodium, potassium or calcium salts. In certain embodiments, the composition includes mono-phosphates (e.g. monobasic, dibasic or tribasic phosphate), P1-6 polyphosphates, Gantrez, or a combination thereof. Still in certain embodiments, the composition includes sodium tripolyphosphate, tetrasodium pyrophosphate, Gantrez, or a combination thereof.

Abrasives:

The compositions of the disclosure (e.g., Composition 1.0 et seq) can include abrasives. Examples of suitable abrasives include silica abrasives, such as standard cleaning silicas, high cleaning silicas, synthetic abrasive silica or any other suitable abrasive silicas. Additional examples of abrasives that can be used in addition to or in place of the silica abrasives include phosphate abrasives, for example, a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal), calcium pyrophosphate, sodium metaphosphate, or potassium metaphosphate; calcium carbonate abrasive; or abrasives such as anhydrous alumina trihydrate, aluminum silicate, calcined alumina, bentonite or other siliceous materials, or combinations thereof. The abrasive is generally present in the compositions of the present invention at a concentration of about 10 to about 40% by weight and preferably about 15 to about 20 or about 30% by weight.

Humectants:

Within certain embodiments of the oral compositions, it is also desirable to incorporate a humectant to prevent the composition from hardening upon exposure to air. Suitable humectants include glycerin, sorbitol, propylene glycol, and polyethylene glycol (e.g., polyethylene glycol having a molecular weight in the range of 200-8000), as well as other polyols and mixtures of these humectants. In one embodiment of the disclosure, the principal humectant is one of glycerin, sorbitol, polyethylene glycol, propylene glycol. One or more humectants may be present at levels of greater than about 25% by weight, such as from about 25 to about 55% by weight, or from about 30 or about 40 to about 50% by weight, based on the total weight of the composition.

Polymers:

Within certain embodiments of the oral compositions (e.g., Composition 1.0 et seq), polymers are included to adjust the viscosity of the formulation or enhance the solubility of other ingredients. Such polymers include polyethylene glycols, polysaccharides (e.g., cellulose derivatives, for example carboxymethyl cellulose (CMC), microcrystalline cellulose or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. In one embodiment, the oral care composition may contain polyvinyl pyrrolidone (PVP). PVP generally refers to a polymer containing vinylpyrrolidone (also referred to as N-vinylpyrrolidone, N-vinyl-2-pyrrolidione and N-vinyl-2-pyrrolidinone) as a monomeric unit.

The compositions of the disclosure (e.g., Composition 1.0 et seq) may include an anionic polymer (e.g., as an antibacterial enhancing agent), for example, in an amount of from 0.05 to 5%. Examples of such agents are disclosed in U.S. Pat. Nos. 5,188,821 and 5,192,531, both of which are incorporated herein by reference in their entirety. These polymers include synthetic anionic polymeric polycarboxylates, such as 1:4 to 4:1 copolymers of maleic anhydride or acid with another polymerizable ethylenically unsaturated monomer, preferably methyl vinyl ether/maleic anhydride. Preferably, the copolymer has a molecular weight (M.W.) of from 30,000 to 1,000,000, such as from 300,000 to 800,000. These copolymers are available, for example, as Gantrez, e.g., AN 139 (M.W. 500,000), AN 119 (M.W. 250,000) and S-97 Pharmaceutical Grade (M.W. 700,000) available from ISP Technologies, Inc., Bound Brook, N.J. 08805. The polymers when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of from 1,000 to 2,000,000, described in U.S. Pat. No. 4,842,847, Jun. 27, 1989 to Zahid, which is incorporated herein by reference in its entirety. Another useful class of polymeric agents includes polyamino acids containing proportions of anionic surface-active amino acids such as aspartic acid, glutamic acid and phosphoserine, e.g. as disclosed in U.S. Pat. No. 4,866,161, issued to Sikes et al., which is also incorporated herein by reference in its entirety.

Thickeners:

Thickeners or gelling agents may be included in the composition (e.g., Composition 1.0 et seq). Suitable examples of thickeners are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. Silica that forms polymeric structures or gels in aqueous media, may be present. Note that these silica thickeners are physically and functionally distinct from the particulate silica abrasives also present in the compositions, as the silica thickeners are very finely divided and provide little or no abrasive action. In certain embodiments, thickening agents are presented in an amount of from about 0.1 to about 15%; from about 0.2, about 0.3 or about 0.4 to about 10%; from about 0.5% to about 1, about 2, about 3, about 4 or about 5%, by weight of the total composition that is used.

Surfactant:

Surfactants or surface active agents may be incorporated in the oral composition (e.g., Composition 1.0 et seq) to provide foaming properties and also to aid in producing a uniform composition in which the ingredients of the composition are evenly distributed. The surfactant may be anionic, cationic, nonionic or zwitterionic (ampholytic) in nature. In some embodiments, a mixture of surfactants are employed, e.g. of different natures. Generally, suitable surfactants are those which are reasonably stable throughout a wide pH range.

Suitable examples of anionic surfactants are water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example, sodium laureth sulfate; higher alkyl aryl sulfonates such as sodium dodecyl benzene sulfonate (sodium lauryl benzene sulfonate) and sodium dodecylbenzen sulfonate; higher alkyl sulfoacetates, such as sodium lauryl sulfoacetate (dodecyl sodium sulfoacetate), higher fatty acid esters of 1, 2-dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In certain embodiments, the anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate, sodium lauroyl sarcosinate and sodium coconut monoglyceride sulfonates are examples of anionic surfactants of this type. In particular embodiments, the anionic surfactant is selected from sodium lauryl sulfate and sodium ether lauryl sulfate. In a particular embodiment, the compositions of the disclosure comprise sodium lauryl sulfate. One or more anionic surfactants may be present in an amount which is effective, e.g., >about 0.01% by weight of the formulation, but not at a concentration which would be irritating to the oral tissue, e.g., <about 10%, and optimal concentrations depend on the particular formulation and the particular surfactant. In one embodiment, one or more anionic surfactants are present in a toothpaste at from about 0.3% to about 4.5% by weight, e.g., about 0.5, 1, to about 2, 3, or 4% by weight, e.g., about 1.84% by weight, based on the total weight of the composition. The compositions of the disclosure may optionally contain mixtures of surfactants, e.g., comprising anionic surfactants and other surfactants that may be anionic, cationic, zwitterionic or nonionic, for example, cocamidopropylbetaine.

Examples of water soluble nonionic surfactants are condensation products of ethylene oxide with various hydrogen containing compounds that are reactive therewith and have long hydrophobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., pluronic materials).

Surfactants are described more fully, for example, in U.S. Pat. No. 3,937,807, to Haefele; and U.S. Pat. No. 4,051,234, to Gieske et al, the disclosures of which are incorporated herein by reference in their entireties.

Whitening Agents:

In some embodiments, a dentifrice composition of the present disclosure further includes a whitening agent. Whitening agents suitable for use in the present invention (e.g., Composition 1.0 et seq) may include any therapeutically effective agent suitable for use in an oral cavity. Suitable whitening agents include, but are not limited to: titanium dioxide, hydrogen peroxide, sodium tripolyphosphate, and the like. In one embodiment, a composition of the present invention further includes titanium dioxide and/or sodium tripolyphosphate.

Pigments and Dyes:

Other components, which may be incorporated in the dentifrice of the present disclosure (e.g., Composition 1.0 et seq), include pigments and dyes. In dental formulations the pigment and dyes may be titanium dioxide coated mica and/or FD. & C grade dyes. The proportion of the pigment will normally be in the range of about 0.05 to about 3% by weight, preferably about 0.1 to about 1.0% by weight. FD. & C grade dyes may be used in appropriate amounts to provide desired colors, e.g., about 0.0001 to about 0.05% by weight, e.g., about 0.002% by weight.

Flavoring Agents:

The oral care compositions of the present disclosure (e.g., Composition 1.0 et seq) may also include a flavoring agent. Suitable flavoring agents include, but are not limited to, essential oils as well as various flavoring aldehydes, esters, alcohols, and similar materials. Examples of the essential oils include oils of spearmint, peppermint, wintergreen, *sassafras*, clove, sage, *eucalyptus*, marjoram, cinnamon, lemon, lime, grapefruit, and orange. Other suitable flavoring agents include such chemicals as menthol, carvone, and anethole. Certain embodiments employ the oils of peppermint and spearmint. The flavoring agent may be incorporated in the oral composition at a concentration of from 0.1 to about 5% by weight e.g., from about 0.5 to about 2.5% by weight.

Compositions according to the present disclosure may be formulated in a suitable dentifrice base, e.g., comprising abrasives, silica abrasives, surfactants, foaming agents, vitamins, polymers, enzymes, humectants, thickeners, additional antimicrobial agents, preservatives, sudsing agents, sweetening agents (such as sodium saccharin), flavorings, aesthetics agents, colorings, and/or combinations thereof. Examples of suitable dentifrice bases are known in the art. Alternatively, the compositions may be formulated as a gel (e.g., for use in a tray). These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference in their entirety.

The present application further discloses methods of using the compositions described herein to for treating or preventing erosion of tooth enamel, plaque and gingivitis. The methods comprise applying any of the compositions as described herein to the teeth, e.g., by brushing, or otherwise administering the compositions to the oral cavity of a subject in need thereof. The compositions can be administered regularly, such as, for example, one or more times per day. In various embodiments, administering the compositions of the present disclosure to a patient can provide one or more of the following benefits: (i) reduce hypersensitivity of the teeth, (ii) reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) increase relative levels of non-cariogenic and/or non-plaque forming bacteria, (ix) reduce or inhibit formation of dental caries, (x) reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues. The disclosure further provides compositions for use in any of the above methods. Further embodiments provide methods wherein at least one tooth is remineralized after administration of a composition as described herein.

EXAMPLES

Example 1: Formula Compositions

Representative Formulation

| Ingredient | Weight % |
| --- | --- |
| Humectants | 25-55 (e.g., 47) |
| Abrasives | 30-40 (e.g. 24) |
| PURIFIED WATER (Free) | 5-15 (e.g. 9) |
| Organic acid salt (e.g. Trisodium Citrate Dihydrate) | 1-10 (e.g. 3.0) |
| Sodium Tripolyphosphate | 0.5-15 (e.g. 3.0) |
| Zinc L-lactate dihydrate | 0.05-10 (e.g. 2.5) |
| Flavors and Colors | 1-10 (e.g. 2.9) |
| Tetrasodium Pyrophosphate | 0.5-15 (e.g 2.0) |
| Anionic Surfactant | 0.01-10 (e.g. 1.8) |
| Polymers | 0.05-5 (e.g. 1.85) |
| Zwitterionic Surfactant | 0.01-10 (e.g. 1.00) |
| Thickeners | 0.1-15 (e.g. 1.6) |
| Organic acid (e.g. Citric Acid) | 0.1-5 (e.g. 0.60) |
| Stannous Fluoride | 0.454 |

Example 2: Demineralization/Remineralization Study

A demineralization/remineralization study of an exemplary composition of the present invention (Example 2), along with a Control, and two comparative commercial compositions (Comparative A, Comparative B), are provided below. The Control composition is identical to Example 2, except that it contains 0.12% stannous fluoride instead of 0.454% stannous fluoride. Comparative Composition A is a commercial toothpaste formulation which contains sodium fluoride, but does not contain either stannous or zinc ion agents. Composition B is a commercial toothpaste formulation in which includes stannous fluoride, zinc lactate and sodium hexametaphosphate. Both commercial comparative compositions lack any carboxylic acid buffer systems. The formulas of Example 2 and Composition B is shown in Table 2 below:

TABLE 2

| Ingredient | Example 2 | Comparative B |
|---|---|---|
| Water and minors (color, flavor) | 11.74 | 9.50 |
| Stannous fluoride | 0.454 | 0.454 |
| Zinc lactate | 2.50 | 2.50 |
| Thickeners | 2.65 | 3.15 |
| Glycerin | 39.69 | 34.65 |
| Abrasive silica | 24.00 | 20.00 |
| Sodium Hexametaphosphate | — | 13.00 |
| Propylene Glycol | 4.00 | 7.00 |
| Trisodium Citrate Dihydrate | 3.00 | — |
| Sodium Tripolyphosphate | 3.00 | — |
| Polyethylene Glycol 600 | 3.00 | 7.00 |
| Tetrasodium Pyrophosphate | 2.00 | — |
| Anionic Surfactant | 1.75 | 1.00 |
| Trisodium Phosphate | — | 1.10 |
| Zwitterionic Surfactant | 1.00 | — |
| Sodium Gluconate | — | 0.65 |
| Anionic Polymer | 0.61 | — |
| Citric Acid | 0.60 | — |

The dentifrices of Example 2, one control sample, and the two comparative examples are tested. During the demineralization/remineralization study, all samples were taken through a 10-day pH cycling protocol. Overall, the teeth were soaked in heated saliva overnight to form a pellicle. They then were treated twice a day with a 1:2 toothpaste slurry and subjected to three 2-minute acid challenges with a 1.0% citric acid solution. Confocal microscopy is used to quantify demineralization of the enamel. The results are shown below, Table 3.

TABLE 3

| Composition | % Mineral Loss |
|---|---|
| Control | 75.56 |
| Comparative A | 71.29 |
| Comparative B | 53.12 |
| Example 2 (SnF and Zn Lactate) | 21.63 |

Teeth treated with the dentifrice composition of Example 2 only show 21.63% mineral loss while the teeth without treatment (control) demonstrate 75.56% mineral loss, and teeth treated with Comparative A and Comparative B demonstrate 71.29%, and 53.12% mineral loss, respectively. Thus, the dentifrice composition of Example 2 demonstrates enhanced protection against mineral loss compared to prior art compositions.

Example 3: Anti-Microbial Test

Anti-microbial properties of the dentifrice compositions of Example 2 and comparative examples were studied in an anaerobic Biofilm model which contains gram-negative anaerobic bacteria on agar enriched with naladixic acid and vancomycin. The bacteria culture is grown on a hydroxyapatite (HAP) disk overnight under anaerobic conditions to first grow the biofilm. The disks are then treated two times per day for five days with the test composition, also under anaerobic conditions. On the fifth day, the HAP disc is treated only once, to allow for regrowth of the biofilm. The HAP disk is then plated 5% sheep's blood and left overnight for colonies to grow. The colonies are then counted and reported as $\log_{10}$ colony-forming units/mL (CFU/mL). The results are shown in Table 3 below.

As illustrated by the data described in Table 4, the exemplary compositions of the present disclosure demonstrate higher antibacterial efficacy than the comparative composition. Test Formula A, performed statistically significantly better than the comparative commercial compositions B, C and D in inhibiting bacterial growth during the test period.

TABLE 4

| Composition | $\log_{10}$ CFU/ml after 8 days |
|---|---|
| Example 2 | 4.29 |
| Comparative D | 5.40 |
| Comparative C | 5.29 |
| Comparative B | 5.56 |

Comparative Composition B is the commercial comparative composition used in the mineral loss test above. Comparative Compositions C and D are similar commercial compositions to B, each of which also contains 0.454% stannous fluoride, 2.5% zinc lactate and sodium hexametaphosphate, and which also lacks a carboxylic acid buffer system As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

What is claimed is:

1. A method of treating or reducing demineralization of teeth in the oral cavity comprising administering an oral care composition to the oral cavity of a subject in need thereof, where the oral care composition, comprises an orally acceptable carrier and:
   zinc lactate, wherein the composition comprises zinc lactate in an amount of about 2.5% by weight of the composition;
   a stannous ion source, wherein the stannous ion source is stannous fluoride present in an amount of from 0.1 to 3% by weight of the oral care composition;
   a phosphate salt, wherein the phosphate salt is selected from tetrasodium pyrophosphate and/or sodium tripolyphosphate, wherein the amount of the phosphate salt is from 1% to 10% by weight of the oral care composition;
a citrate buffer system, wherein the citrate buffer system comprises citric acid and trisodium citrate; and
about 4% propylene glycol.

2. The method of claim 1, wherein the zinc lactate is zinc lactate dihydrate.

3. The method of claim 1, wherein the orally acceptable carrier comprises water from 10 to 40% by weight of the oral care composition.

4. The method of claim 1, which is a single phase composition.

5. The method according to claim 1, wherein the oral care composition comprises:
   a) about 2.5% zinc lactate;
   b) about 3.6% citrate buffer;
   c) about 0.45% stannous fluoride;
   d) about 3% sodium tripolyphosphate (STPP); and
   e) about 2% tetrasodium pyrophosphate (TSPP).

6. The method of claim 1, wherein the oral care composition is a toothpaste or dental gel.

\* \* \* \* \*

UNITED STATES PATENT AND TRADEMARK OFFICE
CERTIFICATE OF CORRECTION

PATENT NO. : 11,253,444 B2
APPLICATION NO. : 16/309402
DATED : February 22, 2022
INVENTOR(S) : Nihal Dogu et al.

It is certified that error appears in the above-identified patent and that said Letters Patent is hereby corrected as shown below:

In the Claims

In Column 13, Line 16, in Claim 5, delete "about".

Signed and Sealed this
Twenty-fourth Day of May, 2022

*Katherine Kelly Vidal*

Katherine Kelly Vidal
*Director of the United States Patent and Trademark Office*